(12) United States Patent
Fujita et al.

(10) Patent No.: US 9,050,000 B2
(45) Date of Patent: Jun. 9, 2015

(54) BIOLOGICAL SIGNAL DETECTOR

(75) Inventors: Etsunori Fujita, Hiroshima (JP); Yumi Ogura, Hiroshima (JP); Naoki Ochiai, Hiroshima (JP); Shinichiro Maeda, Hiroshima (JP); Kosuke Aoi, Hiroshima (JP)

(73) Assignee: Delta Tooling Co., Ltd., Hiroshima-shi (JP)

( * ) Notice: Subject to any disclaimer, the term of this patent is extended or adjusted under 35 U.S.C. 154(b) by 334 days.

(21) Appl. No.: 13/575,417

(22) PCT Filed: Jan. 26, 2011

(86) PCT No.: PCT/JP2011/051413
§ 371 (c)(1),
(2), (4) Date: Oct. 2, 2012

(87) PCT Pub. No.: WO2011/093303
PCT Pub. Date: Aug. 4, 2011

(65) Prior Publication Data
US 2013/0060164 A1 Mar. 7, 2013

(30) Foreign Application Priority Data
Jan. 26, 2010 (JP) ................................. 2010-014870

(51) Int. Cl.
*A61B 7/00* (2006.01)
*A61B 5/024* (2006.01)
(Continued)

(52) U.S. Cl.
CPC ........... *A61B 5/02444* (2013.01); *A61B 5/0816* (2013.01); *A61B 5/6887* (2013.01); *A61B 5/6892* (2013.01); *A61B 2562/0247* (2013.01); *A61B 2562/043* (2013.01)

(58) Field of Classification Search
USPC ................................... 600/528, 586
See application file for complete search history.

(56) References Cited

U.S. PATENT DOCUMENTS 4,715,235 A * 12/1987 Fukui et al. ................ 73/862.68
7,048,697 B1   5/2006 Mitsuru
(Continued)

FOREIGN PATENT DOCUMENTS

EP          0 930 032 A1      7/1999
EP          1 247 488 A1     10/2002
(Continued)

OTHER PUBLICATIONS
Communication pursuant to Rules 70(2) and 70a(2) EPC issued Jul. 9, 2013 in European Patent Application No. 11737016.3.
(Continued)

*Primary Examiner* — Sean Dougherty
*Assistant Examiner* — Daniel Cerioni
(74) *Attorney, Agent, or Firm* — Oblon, McClelland, Maier & Neustadt, L.L.P.

(57) ABSTRACT

A mechanical amplification device includes a three-dimensional knitted material and foam bodies and laminated in the periphery of the three-dimensional knitted material. A mechanical amplification device provided with a film is disposed between the three-dimensional knitted material and the foam bodies and is provided, and a vibration sensor is attached to this mechanical amplification device. Micro vibration on the body surface caused by a human biological signal is propagated to the foam bodies, the film, and the three-dimensional knitted material, and membrane vibration is generated in the foam bodies and the film, while string vibration of a fiber is generated in the three-dimensional knitted material. As a result, the biological signal such as heart rate, respiration, atrial and aortic vibrations and the like can be accurately transmitted.

10 Claims, 11 Drawing Sheets

(51) Int. Cl.
*A61B 5/00* (2006.01)
*A61B 5/08* (2006.01)

(56) References Cited

U.S. PATENT DOCUMENTS

| | | | |
|---|---|---|---|
| 8,251,447 B2 * | 8/2012 | Fujita et al. | 297/284.6 |
| 8,362,882 B2 * | 1/2013 | Heubel et al. | 340/407.1 |
| 2004/0245036 A1 * | 12/2004 | Fujita et al. | 180/272 |
| 2007/0013217 A1 | 1/2007 | Fujita et al. | |
| 2007/0227267 A1 * | 10/2007 | Loeb et al. | 73/862.046 |
| 2011/0148175 A1 | 6/2011 | Fujita et al. | |
| 2011/0251522 A1 | 10/2011 | Fujita et al. | |
| 2012/0130261 A1 * | 5/2012 | Fujita et al. | 600/500 |

FOREIGN PATENT DOCUMENTS

| | | |
|---|---|---|
| EP | 1 743 800 A2 | 1/2007 |
| JP | 10-014888 A | 1/1998 |
| JP | 2000 277182 | 10/2000 |
| JP | 2002 241733 | 8/2002 |
| JP | 2005-074059 A | 3/2005 |
| JP | 2005 347176 | 12/2005 |
| JP | 2007 220608 | 8/2007 |
| JP | 2009 54283 | 3/2009 |
| JP | 2009120849 A * | 6/2009 |
| JP | 2009-120849 * | 11/2010 |
| JP | 2010 258333 | 11/2010 |
| JP | 2010 272610 | 12/2010 |
| WO | WO 2009/142301 A1 | 11/2009 |
| WO | WO 2010/021229 A1 | 2/2010 |

OTHER PUBLICATIONS

Extended European Search Report issued Jun. 20, 2013 in Patent Application No. 11737016.3.

International Search Report Issued Mar. 8, 2011 in PCT/JP11/51265 Filed Jan. 25, 2011.

* cited by examiner

BIOLOGICAL SIGNAL DETECTOR

TECHNICAL FIELD

The present invention relates to a biological signal detector which detects a biological signal of a human being such as respiration, heart rate, atrial and aortic vibrations.

BACKGROUND ART

As a device which detects a biological signal of a human being such as heart rate, respiration, body motion and the like, Patent Literatures 1 to 8 are disclosed, for example. They use a sealed air bag and measures pneumatic fluctuation in the air bag to detect a human biological signal from obtained pneumatic pressure fluctuation data.

CITATION LIST

Patent Literature

Patent Literature 1: Japanese Unexamined Patent Application Publication No. H2-26963
Patent Literature 2: Japanese Unexamined Patent Application Publication No. H11-19056
Patent Literature 3: Japanese Unexamined Patent Application Publication No. 2001-286448
Patent Literature 4: Japanese Patent No. 3242631
Patent Literature 5: Japanese Patent No. 3419732
Patent Literature 6: Japanese Patent No. 3419733
Patent Literature 7: Japanese Patent No. 3495982
Patent Literature 8: Japanese Patent No. 3513497
Patent Literature 9: Japanese Unexamined Patent Application Publication No. 2007-90032

SUMMARY OF THE INVENTION

Technical Problem

The devices disclosed in Patent Literatures 1 to 8 all measure the pneumatic pressure fluctuation in the air bag with a microphone sensor or a pressure sensor. However, vibration on the body surface accompanying respiration or heart rate which is a human biological signal has extremely small amplitude. Thus, a change in the pneumatic pressure in the air bag generated with such small amplitude of the body surface is also extremely small and can be disturbed by noise. It is possible to capture such small pneumatic pressure fluctuation under an environment without an influence of noise or so-called external vibration, but a large amount of the external vibration is captured under the environment of the external vibration. Therefore, if the device is set on a vehicle seat, for example, the external vibration inputted through a vehicle body during running or body motion prevents detection of a human biological signal. Thus, it is extremely difficult to capture vibration with small amplitude such as heart rate or respiration by applying the technology disclosed in Patent Literatures 1 to 8 to a vehicle seat, and only Patent Literature 8 discloses that it is possible to detect body motion of a driver which is a change having large amplitude and causes large pneumatic pressure fluctuation.

On the other hand, the applicant discloses a biological signal detector in which an air bag with a small volume is used for detecting pressure fluctuation and a three-dimensional knitted material having a load characteristic close to the load characteristic of a human muscle is arranged therein as Patent Literature 9. As a seat to be mounted on a vehicle, a seat having a structure that can effectively remove external vibration is employed so that a biological signal with small amplitude such as heart rate and respiration can be detected from pneumatic pressure fluctuation in the air bag by using a special algorithm for processing a detection signal.

According to the technology disclosed in Patent Literature 9, the biological signal such as heart rate, respiration and the like can be detected by using the air bag with a small volume and the special algorithm as described above, but moreover, it is preferable that a micro vibration involved in heart rate, respiration, atrial and aortic vibrations can be detected with greater sensitivity. With the technology of Patent Literature 9, it is necessary to sandwich the three-dimensional knitted material with two plastic films and weld the peripheral edges of the two plastic films by using means such as vibration welding or the like, which causes a problem of a relatively high manufacturing cost. Particularly, in order to apply processing to keep air tightness at a predetermined level or more in a state where the three-dimensional knitted material is inserted therein, a lead wire of a microphone sensor or the like needs to be taken out, requiring skilled work.

The present invention was made in view of the above and has an object to provide a biological signal detector that can detect a biological signal with small amplitude such as heart rate, respiration, atrial and aortic vibrations or the like with greater sensitivity than before and further, has a simple configuration and can be made easily and manufactured with a low cost.

Solution to Problem

In order to solve the above problems, the biological signal detector according to the present invention is characterized in that a mechanical amplification device provided with a three-dimensional knitted material generating string vibration by vibration propagation involved in a human biological signal and a plate-shaped foam body stacked on at least either one of the front side and the back side of the three-dimensional knitted material and generating membrane vibration by the vibration propagation involved in the human biological signal, and converting the vibration involved in the human biological signal to amplified solid vibration by a superposing action of the string vibration and the membrane vibration; and a vibration sensor attached to the mechanical amplification device for detecting the amplified solid vibration are provided.

It is preferable that the biological signal detector of the present invention further has a configuration in which the mechanical amplification device has a film laminated between the three-dimensional knitted material and the plate-shaped foam body, and the membrane vibration of the film is further superposed.

It is preferable that the mechanical amplification device is further provided with a three-dimensional knitted material supporting member in which an arrangement through hole for arranging the three-dimensional knitted material is formed. In a state where the three-dimensional knitted material is arranged in the arrangement through hole, the film is laminated on at least either one of the front side and the back side of the three-dimensional knitted material, a peripheral edge portion is fixed to the three-dimensional knitted material supporting member, and the plate-shaped foam body is stacked through the film.

The plate-shaped foam body is preferably a bead foam body. Moreover, the three-dimensional knitted material supporting member is preferably a bead foam body formed having a plate shape. The bead foam body is preferably a foam molded body by a bead method of a resin containing at least any one of polystyrene, polypropylene, and polyethylene. The bead foam body is preferably formed having a thickness not more than an average diameter of the bead.

The three-dimensional knitted material preferably has a thickness larger than that of the bead foam body constituting the three-dimensional knitted material supporting member. The three-dimensional knitted material has a spring constant close to a spring constant obtained from the load-deflection characteristic of a human muscle in a load-deflection characteristic within a range of a load up to 100 N when being pressurized by a pressure plate having a diameter of 30 mm or a diameter of 98 mm.

It is preferable that the three-dimensional knitted material includes a pair of ground knitted fabrics arranged separately from each other and a large number of connecting yarns which reciprocate between the pair of ground knitted fabrics and connect the both, and the connecting yarn is a monofilament. The three-dimensional kitted material may include a pair of ground knitted fabrics arranged separately from each other and a large number of connecting yarns reciprocating between the pair of ground knitted fabrics and connect the both, and the connecting yarn may be a multifilament.

A sensing portion of the vibration sensor is preferably fixed to the three-dimensional knitted material, the plate-shaped foam body or the film. The vibration sensor is preferably a microphone sensor.

The biological signal detector of the present invention is preferably used in bedding or a seat structure by being attached to a range corresponding to the back part of a human being.

Advantages of the Invention

The present invention has the mechanical amplification device provided with the three-dimensional knitted material and the plate-shaped foam body stacked on the periphery of the three-dimensional knitted material, preferably the mechanical amplification device in which a film is disposed between the three-dimensional knitted material and the plate-shaped foam body and is configured such that the vibration sensor is attached to this mechanical amplification device. The micro vibration on the body surface by the human biological signal such as heart rate, respiration, atrial and aortic vibrations and the like is propagated to the plate-shaped foam body, the film, and the three-dimensional knitted material, and the membrane vibration is generated in the plate-shaped foam body and the film, while the string vibration of the fiber is generated in the three-dimensional knitted material. Moreover, the three-dimensional knitted material is composed of the connecting yarn disposed between the pair of ground knitted fabrics and is provided with the load-deflection characteristic close to the load-deflection characteristic of a human muscle. Therefore, by making the load-deflection characteristic of the mechanical amplification device including the three-dimensional knitted material close to that of the muscle and arranging the mechanical amplification device adjacent to the muscle, a difference between internal and external pressures between the muscle and the three-dimensional knitted material becomes equal, and a biological signal such as heart rate, respiration, atrial and aortic vibrations and the like can be transmitted accurately, whereby the string vibration can be generated in a fiber (or particularly the connecting yarn) constituting the three-dimensional knitted material. Moreover, the plate-shaped foam body stacked on the three-dimensional knitted material, preferably a bead foam body can easily generate membrane vibration in each bead due to flexible elasticity and small density of the bead. The film can easily generate membrane vibration since a predetermined tension is generated by means of fixation of the peripheral edge portion and elastic support by the three-dimensional knitted material close to the load-deflection characteristic of a human muscle. That is, according to the present invention, the membrane vibration is generated in the plate-shaped foam body or the film in the mechanical amplification device having the load-deflection characteristic close to the load-deflection characteristic of the muscle by a biological signal such as heart rate, respiration, atrial and aortic vibrations and the like, and the string vibration is generated in the three-dimensional knitted material having the load-deflection characteristic close to the load-deflection characteristic of the human muscle. The string vibration of the three-dimensional knitted material influences the membrane vibration of the film and the like again, and these vibrations act in a superposed manner. As a result, the vibration inputted from the body surface with the biological signal is directly detected by the vibration sensor as solid vibration amplified by superposition of the string vibration and the membrane vibration.

If the pneumatic pressure fluctuation in the sealed bag is detected as in the prior-art technology, since the volume and the pressure are inversely proportional, the pressure fluctuation cannot be easily detected unless the volume of the sealed bag is made small. In contrast, according to the present invention, instead of the pneumatic pressure fluctuation, the amplified solid vibration propagated to the mechanical amplification device (the three-dimensional knitted material, the plate-shaped foam body, and the film) is detected as described above. Thus, the capacity (volume) is rarely limited from the viewpoint of detection sensitivity, and the vibration with small amplitude involved in heart rate, respiration, atrial and aortic vibrations and the like can be detected with good sensitivity. Accordingly, the device can handle people with various physical sizes. As described above, the present invention is suitable as a biological signal detector under an environment such as a vehicle seat used by people with various physical sizes and into which various external vibrations are inputted. Moreover, since it is not necessary to form a sealed structure, a manufacturing process is simplified and a manufacturing cost can be lowered, which is suitable for mass production.

DESCRIPTION OF EMBODIMENTS

Figure 1:
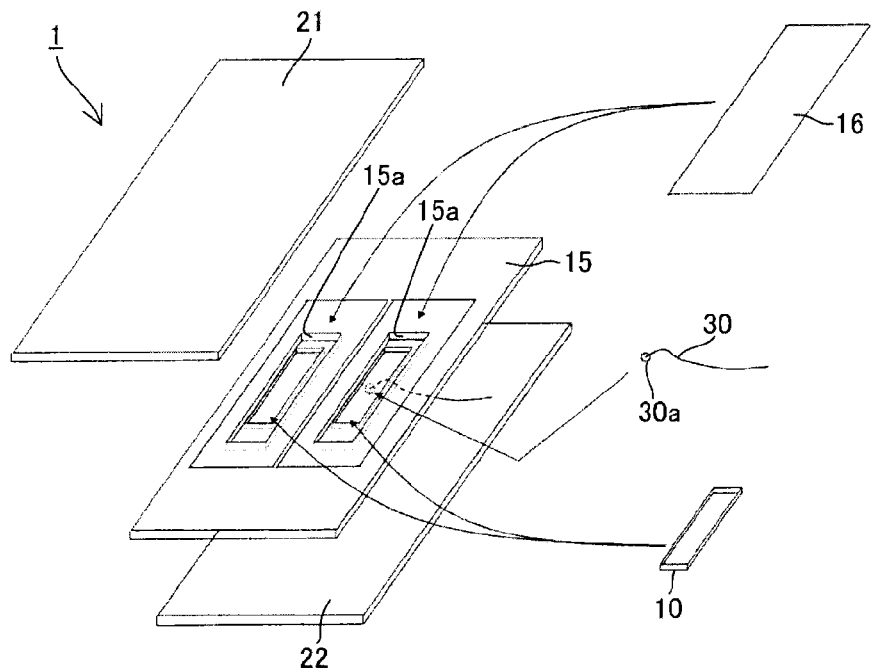
FIG. 1 is an exploded perspective diagram illustrating a configuration of a biological signal detector according to an embodiment of the present invention.

The present invention will be described below in further detail on the basis of an embodiment of the present invention illustrated in the drawings. FIG. 1 is a configuration diagram illustrating a biological signal detector 1 according to this embodiment. The biological signal detector 1 includes a three-dimensional knitted material 10, a three-dimensional knitted material supporting member 15, a film 16, plate-shaped foam bodies 21 and 22, and a vibration sensor 30.

The three-dimensional knitted material 10 is, as disclosed in Japanese Unexamined Patent Application Publication No. 2002-331603, for example, a knitted fabric having a three-dimensional structure having a pair of ground knitted fabrics arranged separately from each other and a large number of connecting yarns reciprocating between the pair of ground knitted fabrics and connecting the both.

One of the ground knitted fabrics is formed of a flat knitted fabric composition (fine stitch) which is continuous both in a wale direction and a course direction from a yarn obtained by twisting a monofilament, for example, while the other ground knitted fabric is formed having a knitted structure having a honeycomb-shaped (hexagonal) mesh from a yarn obtained by twisting a short fiber, for example. It is needless to say that the knitted fabric composition is optional and its combination is also optional such that a knitted fabric composition other than the fine-stitch composition or the honeycomb-shape can be employed, alternatively, the fine-stitch composition can be employed for the both. The connecting yarn is knitted between the two ground knitted fabrics so that the one ground knitted fabric and the other ground knitted fabric maintain a predetermined interval. In this embodiment, since the solid vibration of the three-dimensional knitted material or particularly the string vibration of the connecting yarn is to be detected, the connecting yarn is preferably formed of a monofilament, but the connecting yarn may also be formed of a multifilament in order to adjust a resonance frequency in accordance with the type of a biological signal to be sampled.

Moreover, the three-dimensional knitted material 10 is preferably provided with a load-deflection characteristic in a thickness direction within a range up to the load of 100 N when being placed on a measuring plate and pressurized by a pressure plate having a diameter of 30 mm or a diameter of 98 mm and with a spring constant close to the load-deflection characteristic of a muscle in the buttocks of a human being. Specifically, it is preferable to use the material having the spring constant within a range of 0.1 to 5 N/mm when being pressurized by a pressure plate having the diameter of 30 mm or the material having the spring constant within a range of 1 to 10 N/mm when being pressurized by a pressure plate having the diameter of 98 mm. By means of approximation to the load-deflection characteristic of the muscle in the buttocks of a human being, the three-dimensional knitted material is balanced with the muscle, and when a biological signal of heart rate, respiration, atrial and aortic vibrations and the like is propagated, the three-dimensional knitted material generates the vibration similar to that in the human muscle, and the biological signal can be propagated without large attenuation.

As such three-dimensional knitted material, the following may be used, for example. Each of the three-dimensional knitted materials can be used by being stacked in plural as necessary.

(1) Product number: 49076D (by Suminoe Textile Co., Ltd.) Material:

Ground knitted fabric on the front side: Twisted yarn of polyethylene terephthalate fiber false twisted yarn of 300 decitex/288f and polyethylene terephthalate fiber false twisted yarn of 700 decitex/192f Ground knitted fabric on the back side: Combination of polyethylene terephthalate fiber false twisted yarn of 450 decitex/108f and polytrimethylene terephthalate monofilament of 350 decitex/1f Connecting yarn: polytrimethylene terephthalate monofilament of 350 decitex/1f (2) Product number: 49011D (by Suminoe Textile Co., Ltd.) Material:

Ground knitted fabric (warp) Polyethylene terephthalate fiber false twisted yarn of 600 decitex/192f Ground knitted fabric (weft) Polyethylene terephthalate fiber false twisted yarn of 300 decitex/72f Connecting yarn: polyethylene terephthalate monofilament of 800 decitex/1f (3) Product number: 49013D (by Suminoe Textile Co., Ltd.) Material:

Ground knitted fabric on the front side: Two twisted yarns of polyethylene terephthalate fiber false twisted yarn of 450 decitex/108f Ground knitted fabric on the back side: Two twisted yarns of polyethylene terephthalate fiber false twisted yarn of 450 decitex/108f Connecting yarn: polytrimethylene terephthalate monofilament of 350 decitex/1f (4) Product number: 69030D (by Suminoe Textile Co., Ltd.) Material:

Ground knitted fabric on the front side: Two twisted yarns of polyethylene terephthalate fiber false twisted yarn of 450 decitex/144f Ground knitted fabric on the back side: Combination of polyethylene terephthalate fiber false twisted yarn of 450 decitex/144f and polytrimethylene terephthalate monofilament of 350 decitex/1f Connecting yarn: polytrimethylene terephthalate monofilament of 350 decitex/1f (5) Product number: T24053AY5-1S by Asahi Kasei Fibers Corporation The plate-shaped foam bodies 21 and 22 are preferably formed of bead foam bodies. As the bead foam body, a foam molded body molded by a bead method of a resin containing at least any one of polystyrene, polypropylene, and polyethylene can be used. The plate-shaped foam bodies 21 and 22 made of bead foam bodies propagate a biological signal with micro amplitude as membrane vibration by means of characteristics of a spherical resin film formed by foams constituting individual fine beads. This membrane vibration is transmitted as string vibration to the three-dimensional knitted material, the membrane vibration and the string vibration are superposed with each other, and the biological signal is detected by the vibration sensor 30 which will be described later as mechanical vibration amplified by superposition of the membrane vibration and the string vibration. Therefore, detection of the biological signal is facilitated.

If the plate-shaped foam bodies 21 and 22 are to be formed of bead foam bodies, a foaming factor is preferably within 25 to 50 times and the thickness is formed at an average diameter of a bead or less. For example, if the average diameter of a bead of 30-times foaming is approximately 4 to 6 mm, the plate-shaped foam bodies 21 and 22 are sliced to the thickness of approximately 3 to 5 mm. As a result, flexible elasticity is given to the plate-shaped foam bodies 21 and 22, and solid vibration resonant with vibration with small amplitude can easily occur.

Here, as the three-dimensional knitted material 10, a strip-shaped material having a width within a range of 40 to 100 mm and a length within a range of 100 to 300 mm is used. In this embodiment, in order to reduce a sense of discomfort when the back part of a human being is in contact the device, two strips are disposed on a target, sandwiching a portion corresponding to the spine. It is preferable that the three-dimensional knitted material 10 is configured to be supported by the three-dimensional knitted material supporting member 15 as illustrated in FIG. 1 so that the three-dimensional knitted materials 10 can be arranged at predetermined positions easily. The three-dimensional knitted material supporting member 15 is molded having a plate shape, and two vertically long through holes 15a and 15a for arrangement are formed at symmetrical positions sandwiching the portion corresponding to the spine. The three-dimensional knitted material supporting member 15 is preferably composed of the bead foam bodies formed having a plate shape similarly to the above-described plate-shaped foam bodies 21 and 22. The preferable foaming factor and range of thickness if the three-dimensional knitted material supporting member 15 is formed of a bead foam body are the same as those of the above-described plate-shaped foam bodies 21 and 22. However, the thicknesses of the plate-shaped foam bodies 21 and 22 stacked above and below the three-dimensional knitted materials 10 and 10 are preferably smaller than the thickness of the three-dimensional knitted material supporting member 15 in order that the membrane vibration is generated more remarkably by the biological signal.

In a state where the two three-dimensional knitted materials 10 and 10 are inserted and arranged in the through holes 15a and 15a for arrangement formed in the three-dimensional knitted material supporting member 15, the films 16 and 16 are laminated on the front side and the back side of the three-dimensional knitted materials 10 and 10. In this embodiment, the peripheral edge portions of the films 16 and 16 are bonded and laminated on the peripheral edge portions of the through holes 15a and 15a for arrangement. The formed positions of the through holes 15a and 15a for arrangement (that is, the disposed positions of the three-dimensional knitted materials 10 and 10) are preferably set to positions corresponding to regions where vibration caused by motion involved in pumping of atrium and aorta (particularly "descending aorta") and motion of an aortic valve can be detected. As a result, the three-dimensional knitted materials 10 and 10 are sandwiched by the plate-shaped foam bodies 21 and 22 on the upper and lower surfaces, the peripheral edge portions are surrounded by the three-dimensional knitted material supporting member 15, and the plate-shaped foam bodies 21 and 22 and the three-dimensional knitted material supporting member 15 function as a resonance box (resonant box).

Moreover, it is preferable that the three-dimensional knitted materials 10 and 10 are thicker than the three-dimensional knitted material supporting member 15 in use. That is, such a thickness relationship is realized that, when the three-dimensional knitted materials 10 and 10 are arranged in the through holes 15a and 15a for arrangement, the front surfaces and the back surfaces of the three-dimensional knitted materials 10 and 10 protrude from the through holes 15a and 15a for arrangement. As a result, when the peripheral edge portions of the films 16 and 16 are bonded to the peripheral edge portions of the through holes 15a and 15a for arrangement, the three-dimensional knitted materials 10 and 10 are pressed in the thickness direction. Therefore, a tensile force caused by a reaction force of the films 16 and 16 is generated, and the solid vibration (membrane vibration) can easily occur in the films 16 and 16. On the other hand, preliminary compression occurs also in the three-dimensional knitted materials 10 and 10, and a tension caused by the reaction force is generated also in the connecting yarn maintaining the thickness form of the three-dimensional knitted materials, thereby the string vibration can easily occur. The films 16 and 16 are preferably provided on both sides of the front sides and the back sides of the three-dimensional knitted materials 10 and 10, but it is possible to configure such that the film 16 is provided on at least either one of them.

Since the connecting yarn of the three-dimensional knitted materials 10 and 10 is extended between the pair of ground knitted fabrics, it becomes a long string wound in a so-called coil shape, and the films 16 and 16 and the plate-shaped foam bodies 21 and 22 functioning as the resonance box (resonant box) are disposed at upper and lower node points. Since the biological signal represented by heart rate fluctuation has a low frequency, it is amplified by the resonance system provided with the long string and the large number of node points. That is, the string vibration of the connecting yarn causes the membrane vibration of the films 16 and 16 and the membrane vibration of the beads of the plate-shaped foam bodies 21 and 22 to be generated through the large number of node points, whereby they are superposed in action and are amplified. The interval between the node points of the connecting yarn of the three-dimensional knitted materials, that is, the arrangement density of the connecting yarn is higher the better.

Figure 2:
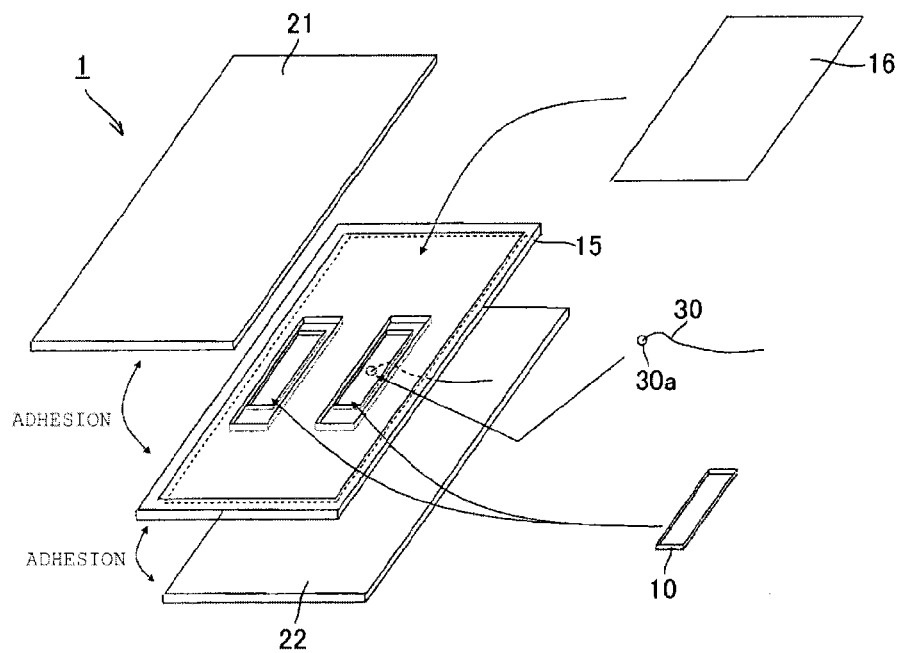
FIG. 2 is an exploded perspective diagram illustrating a film in use according to another form in the biological signal detector in FIG. 1.

Moreover, it is possible to configure such that the films 16 and 16 can be arranged on the front side and the back side of the three-dimensional knitted materials 10 and 10 only by bonding the films 16 and 16 on the plate-shaped foam bodies 21 and 22 side in advance to be integrated and by stacking the plate-shaped foam bodies 21 and 22 on the three-dimensional knitted material supporting member 15. However, in order to give the preliminary compression to the three-dimensional knitted materials 10 and 10, the films 16 and 16 are preferably fastened to the surface of the three-dimensional knitted material supporting member 15 as described above. Moreover, instead of disposition of the films in correspondence with each three-dimensional knitted material 10 as in FIG. 1, it is possible to use the film 16 having a size that can cover both the two three-dimensional knitted materials 10 and 10 as illustrated in FIG. 2.

As the films 16 and 16, a plastic film made of polyurethane elastomer (product number "DUS605-CDR" by Sheedom Co., Ltd., for example) is preferably used in order to capture heart rate fluctuation, for example. However, if natural frequencies of the films 16 and 16 match, the membrane vibration is generated by resonance and thus, the above is not limiting but those having the natural frequency according to the target to be sampled (heart rate, respiration, atrial and aortic vibrations and the like) are preferably used. For example, as will be illustrated in a test example which will be described later, a material with small stretch properties such as an unwoven cloth made of thermoplastic polyester (a biaxial woven fabric (warp: 20 fibers/inch, weft: 20 fibers/inch) formed from a polyethylene naphthalate (PEN) fiber (1100 dtex) by Teijin, for example) can be also used. Moreover, an elastic fiber unwoven cloth having an elongation degree of 200% or more and a recovery rate at 100%-elongation is 80% or more (product name "Espansione" by KB Seiren Ltd., for example) can be also used, for example.

The vibration sensor 30 is fastened and disposed on either one of the three-dimensional knitted materials 10 before the above-described films 16 and 16 are laminated. The three-dimensional knitted material 10 is composed of a pair of ground knitted fabrics and the connecting yarn, and since the string vibration of each connecting yarn is transmitted to the films 16 and 16 and the plate-shaped foam bodies 21 and 22 through the node points with the ground knitted fabrics, the vibration sensor 30 is preferably fastened to the surface of the three-dimensional knitted material 10 (surface of the ground knitted fabric) at a sensing portion 30a. As the vibration sensor 30, a microphone sensor or particularly a capacitor-type microphone sensor is preferably used. In this embodiment, since it is not necessary to consider sealing performance at a portion where the microphone sensor is arranged (that is, the through hole 15a for arrangement in which the three-dimensional knitted material 10 is arranged), a lead wire of the microphone sensor can be wired easily. In this embodiment, as described above, the vibration on the body surface through the muscle of a human being involved in the biological signal is propagated not only to the three-dimensional knitted material 10 but also to the plate-shaped foam bodies 21 and 22 and the film 16, and they are vibrated (string vibration, membrane vibration), the superposed and amplified. Thus, the vibration sensor 30 can fix the sensing portion 30a not only to the three-dimensional knitted material 10 but also to the plate-shaped foam bodies 21 and 22 and the film 16 constituting a vibration transmission path. In this embodiment, since the three-dimensional knitted material 10, the three-dimensional knitted material supporting member 15, the plate-shaped foam bodies 21 and 22, and the film 16 mechanically amplify the biological signal, they constitute the mechanical amplification device.

Figure 3:
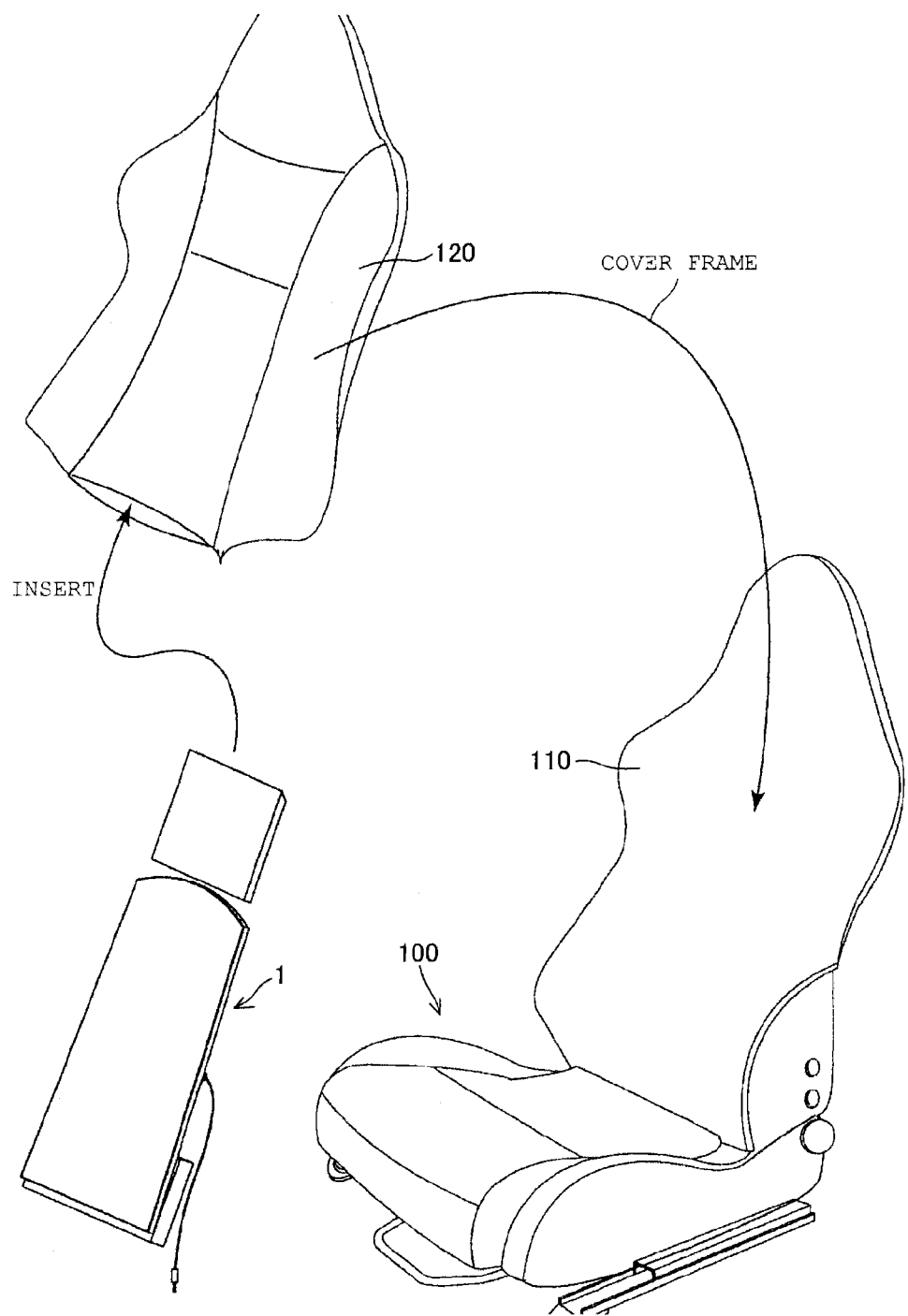
FIG. 3 is a diagram illustrating a process of arranging the biological signal detector in FIG. 1 in an automobile seat.

The biological signal detector 1 described above is arranged inside a seat cover 120 covering a seatback frame 110 of the vehicle seat 100 as illustrated in FIG. 3, for example. In order to facilitate an arrangement work, the three-dimensional knitted material 10, the three-dimensional knitted material supporting member 15, the film 16, the plate-shaped foam bodies 21 and 22, the vibration sensor 30 and the like constituting the biological signal detector 1 are preferably unitized in advance.

Test Example 1

Load-Deflection Characteristics of Biological Signal Detector 1

The biological signal detector 1 of the above-described embodiment was placed on a measuring plate, a spot where the three-dimensional knitted material 10 was arranged was pressurized by a pressure plate having a diameter of 30 mm, and the load-deflection characteristics were examined. As the plate-shaped foam bodies 21 and 22 and the three-dimensional knitted material supporting member 15, a bead foam body having an average bead diameter of approximately 5 mm and sliced to the thickness of 3 mm was used. The three-dimensional knitted material 10 was a product made by Suminoe Textile Co., Ltd., the product number: 49011D and having a thickness of 10 mm. As the film 16, a product made by Sheedom Corporation, the product number of "DUS605-CDR" was used (film specification). Moreover, the biological signal detector 1 of the embodiment was laminated on the back side of the product name "Twin Lumbar" made by Delta Tooling, which is a drive cushion formed from a three-dimensional knitted material having an excellent external vibration removing effect, the laminated body was placed on the measuring plate in that state, and the load-deflection characteristics were measured similarly.

Regarding the biological signal measuring device 1 (PEN specification) manufactured by using a polyethylene terephthalate (PEN) fiber by Teijin as the film 16 and by disposing it so as to cover both the two three-dimensional knitted materials 10 and 10, as illustrated in FIG. 2, and the biological signal measuring device 1 (Espansione specification) manufactured by using the product name "Espansione" by KB Seiren Ltd. as the film 16 and by disposing it so as to cover both the two three-dimensional knitted materials 10 and 10, as illustrated in FIG. 2, the load-deflection characteristics were measured similarly to the above. The result is illustrated in FIG. 4.

Figure 4:
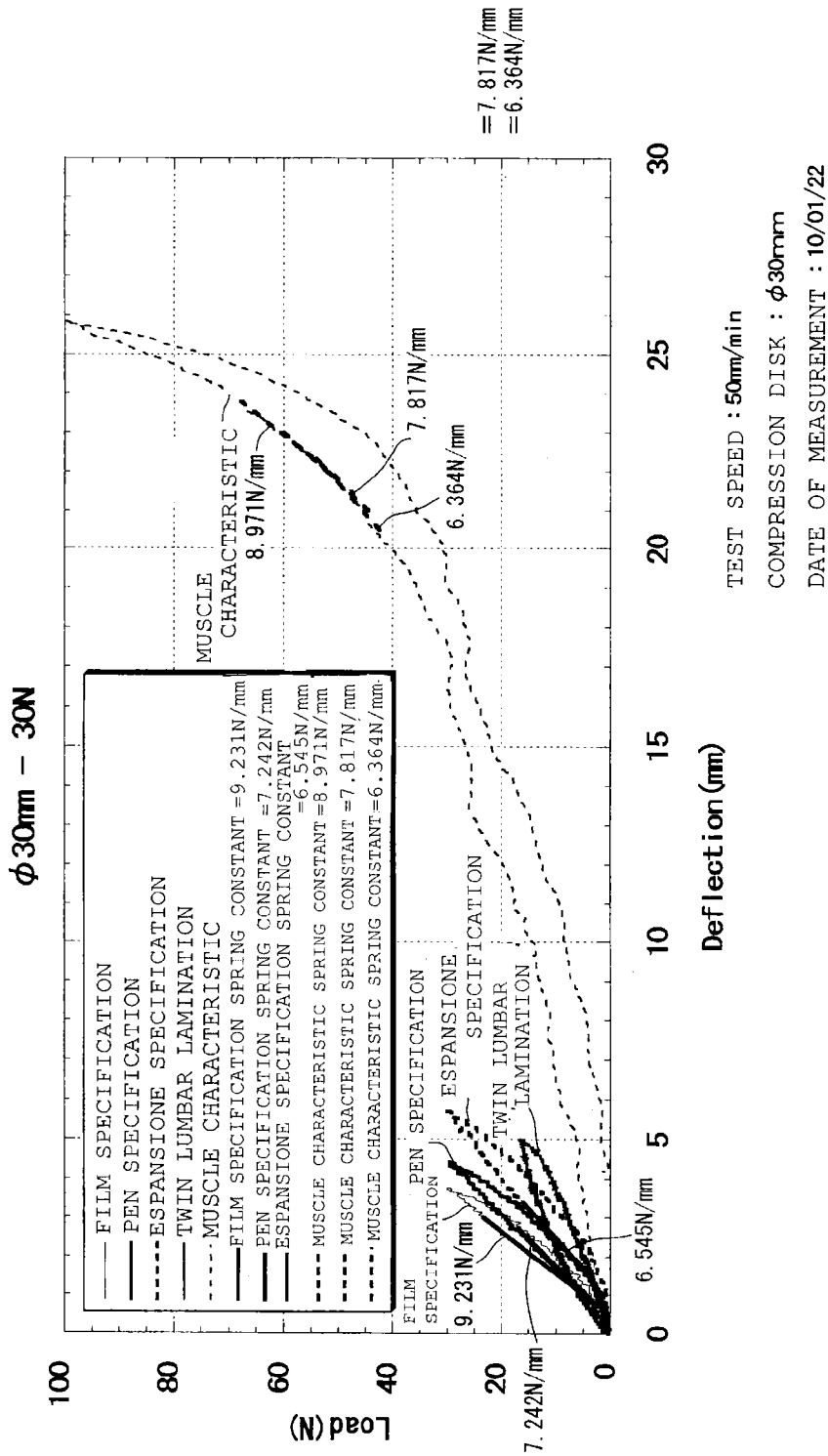
FIG. 4 is a diagram illustrating a load-deflection characteristic of the biological signal detector.

As illustrated in FIG. 4, the biological signal detector 1 of the embodiment had a spring constant within a range up to the load of 30N was 6 to 10 N/mm and that was substantially the same as the spring constant in the load range of 40 to 60 N of the load-deflection characteristics of the muscle on the back part. Moreover, in a state where it was laminated on the product name "Twin Lumbar", the spring constant was further lower and became extremely close to the load-deflection characteristics within the load range around 10 N of the load-deflection characteristics of the muscle of the back part of a human being. Therefore, by using the biological signal measuring device 1 of this embodiment and by covering it with a drive cushion made of a three-dimensional knitted material similarly to the product name "Twin Lumbar" formed from the three-dimensional knitted material or a seat cover made of the three-dimensional knitted material, it is known that a difference between a pressure generated by vibration of the back part muscle of a human being (internal pressure) and a pressure involved in compression and recovery of the three-dimensional knitted material (external pressure) no longer exists, and the heart rate, respiration, atrial and aortic vibrations and the like can be easily propagated as solid vibration.

Test Example 2

Comparison of Presence of Film

Figure 5:
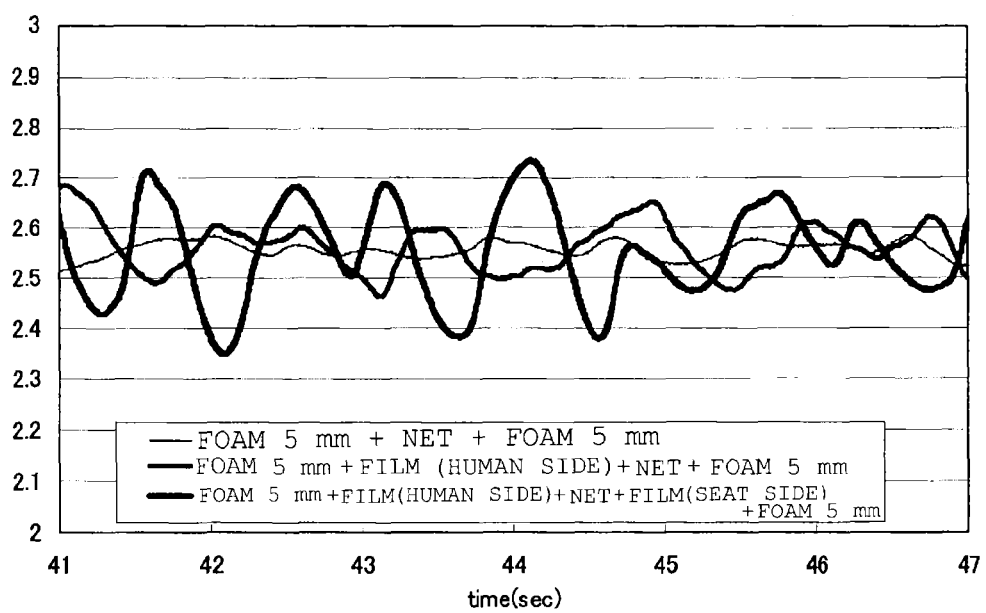
FIG. 5 is a diagram illustrating an output original waveform when a biological signal is measured by the biological signal detector.

The biological signal measuring device 1 employing a material made of a bead foam body having a thickness of 5 mm instead of the plate-shaped foam bodies 21 and 22 made of a bead foam body having a thickness of 3 mm and the three-dimensional knitted material supporting member 15 was manufactured. This was set on a seatback made of resin, a subject was seated, and a biological signal was measured. The device was set on such a region that the three-dimensional knitted material 10 can detect vibration generated by motion involved in pumping of the atrium and aorta (particularly, the "descending aorta") and motion of an aortic valve. FIG. 5 illustrates an output original waveform of the vibration sensor 30 at that time. In FIG. 5, the phrase "FOAM 5 mm+FILM (HUMAN SIDE)+NET+FILM (SEAT SIDE)+FOAM 5 mm" has the completely same structure as the biological signal detector 1 illustrated in FIG. 1, the phrase "FOAM 5 mm+FILM (HUMAN SIDE)+NET+FOAM 5 mm" has the structure obtained by removing the film on the seatback side from the structure in FIG. 1, and the phrase "FOAM 5 mm+NET+FOAM 5 mm" has the structure obtained by removing the both films on the human side and the seat back side from the structure in FIG. 1.

In all cases, the biological signal (vibration of the aorta involved in pumping) is captured, but as compared with the case where the film is not arranged, amplitude in the case where the film is disposed only on the side in contact with a human being is larger, and moreover, if the film is arranged on the both sides of the three-dimensional knitted material 10, the amplitude becomes much larger. Thus, it is known that the amplification effect realized by combination with the membrane vibration of the film 16 is high.

Test Example 3

Comparison Between Biological Signal Measuring Device in this Embodiment and Biological Signal Detector of Prior-Art Air-Bag Type The biological signal detector 1 used in the test example 1 (the type using the product number "DUS605-CDR" by Sheedom Co., Ltd. as the film 16) was stacked on the back side of the product name "Twin Lumbar" made by Delta Tooling which is a drive cushion formed of the three-dimensional knitted material having an excellent external vibration removing effect and placed on the measuring plate in that state, and the load-deflection characteristics were measured similarly.

Figure 6A:
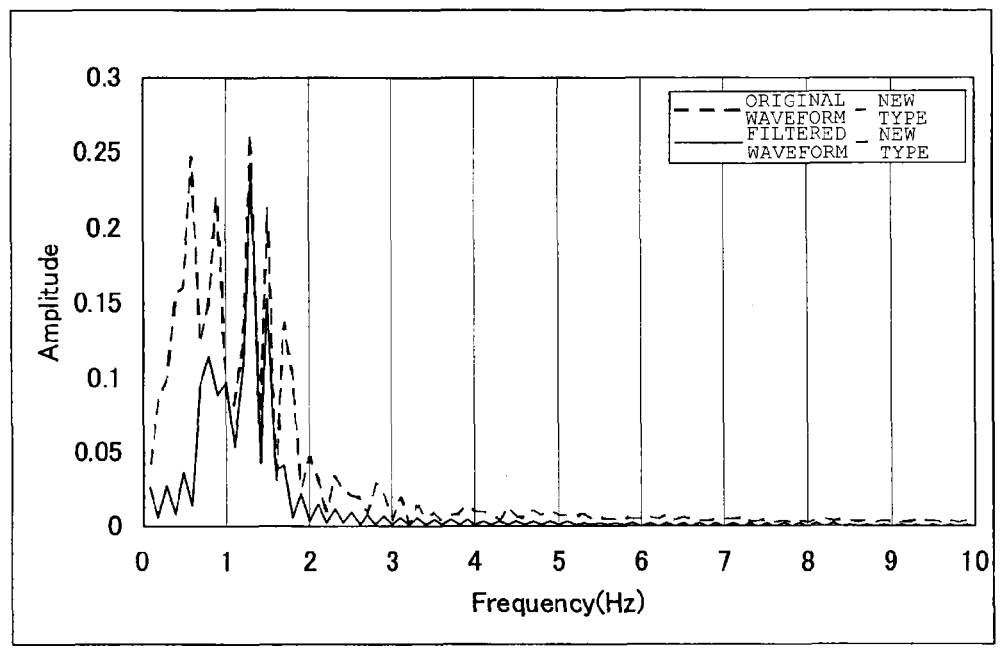
FIG. 6(A) is a diagram illustrating a frequency analysis result of an original waveform outputted from a vibration sensor 30 in a biological signal measuring device of the embodiment and a waveform (filtered waveform) obtained by removing noise such as a body motion component and the like from the original waveform by filtering.

Moreover, the biological signal measuring device 1 manufactured by using a polyethylene naphthalate (PEN) fiber by Teijin as the film 16 and by disposing it so as to cover both the two three-dimensional knitted materials 10 and 10, as illustrated in FIG. 2, and the biological signal measuring device 1 manufactured by using the product name "Espansione" by KB Seiren Ltd. as the film 16 and by disposing it so as to cover both the two three-dimensional knitted materials 10 and 10, as illustrated in FIG. 2, were stacked on the back side of the product name "Twin Lumbar" made by Delta Tooling and attached to a front passenger seat of a vehicle and the actual-vehicle running test was conducted. The device was set on such a region that the three-dimensional knitted material 10 can detect vibration generated by motion involved in pumping of the atrium and aorta (particularly, the "descending aorta") and motion of an aortic valve. FIG. 6(A) illustrates a frequency analysis result of an original waveform outputted from the vibration sensor 30 at that time and a waveform (filtered waveform) obtained by removing the noise such as a body motion component and the like from the original waveform by filtering. The subject was the same as that in the test example 2, and the heart rate of this subject during activity metabolism is approximately 70 times a minute on an average, that is, approximately 1.3 Hz. From FIG. 6(A), it can be observed that the biological signal measuring device 1 used in the test example 1 has the highest peak in the vicinity of 1.2 to 1.4 Hz in the original waveform, while the noise in the vicinity of 0.5 Hz and 0.9 Hz is removed in the filtered waveform, which has a clear peak in the vicinity of 1.2 to 1.4 Hz, and that the atrial and aortic vibration including a heart rate component was reliably detected.

Figure 6B:
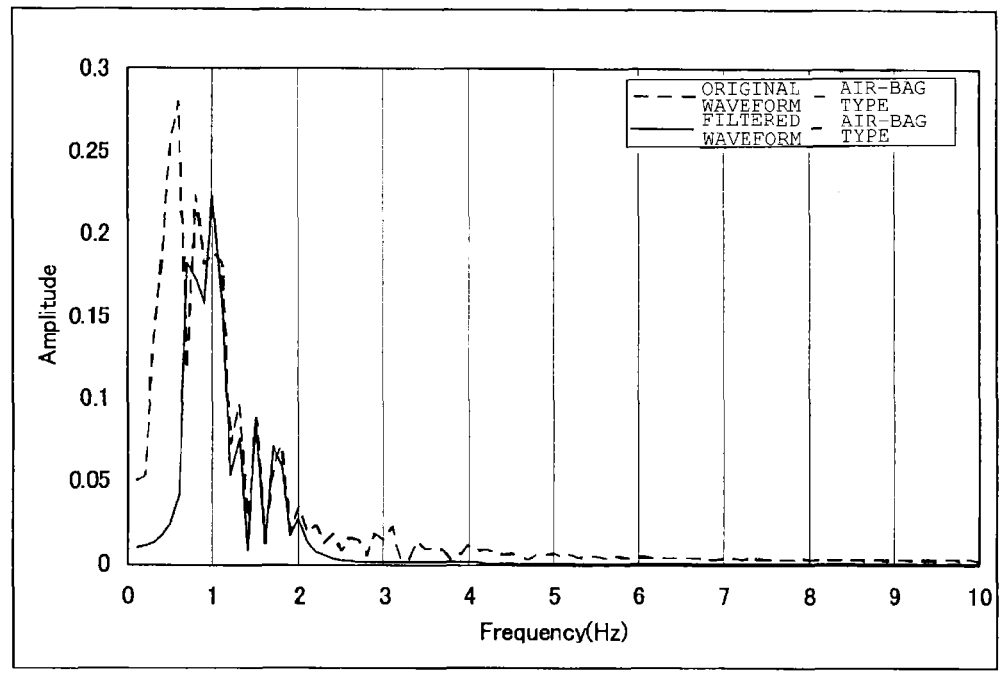
FIG. 6(B) is a diagram illustrating a frequency analysis result of an original waveform outputted from a sensor in a prior-art air-bag type biological signal detector and a waveform (filtered waveform) obtained by removing the noise such as a body motion component and the like from the original waveform by filtering.

On the other hand, a prior-art air-bag type biological signal detector was manufactured by using two films of the product number "DUS605-CDR" by Sheedom Co., Ltd. by positioning the three-dimensional knitted material inside, and further by sandwiching a tube between the two films and sealing the peripheral edge by vibration welding. A capacitor-type microphone sensor was arranged in the tube, and pneumatic pressure fluctuation in the sealed air bag was measured. This air-bag type biological signal detector is stacked on the back side of the product name "Twin Lumbar" made by Delta Tooling and attached to a driver seat of a vehicle similarly to the above and the actual-vehicle running test was conducted. FIG. 6(B) illustrates a frequency analysis result of an original waveform outputted from the microphone sensor at that time and a waveform (filtered waveform) obtained by removing the noise such as a body motion component and the like from the original waveform by filtering. As a result, the original waveform has a peak also in the vicinity of 1.2 Hz in addition to 0.5 Hz, 0.8 Hz, and 1.0 Hz, while the filtered waveform has a peak in the vicinity of 0.8 Hz, 1.0 Hz, and 1.2 Hz, and the highest peak among them was 1.0 Hz. That is, in the case of the air bag type, the resonance frequency was 1.0 Hz which was shifted from 1.2 to 1.4 Hz which is the heart rate component of the subject during activity metabolism. Therefore, the biological signal detector 1 of this embodiment coincided more with the purpose of detecting the biological signal component mainly of the pulse wave of the heart (including the atrial and aortic vibrations) and had more excellent sensitivity than the prior-art air-bag type.

Test Example 4

Comparison of Types of Film

Following three biological signal measuring devices 1 manufactured in the test example 1:

The biological signal measuring device 1 manufactured by disposing the product number "DUS605-CDR" by Sheedom Co., Ltd. as the film 16 on the both sides of each of the two three-dimensional knitted materials 10 and 10 as illustrated in FIG. 1 (noted as "FILM BOTH SIDES" in the figure);

the biological signal measuring device 1 manufactured by using a polyethylene naphthalate (PEN) fiber by Teijin as the film 16 and by disposing it on the both sides of the three-dimensional knitted materials so as to cover both the two three-dimensional knitted materials 10 and 10 as illustrated in FIG. 2 (noted as "PEN BOTH SIDES" in the figure); and the biological signal measuring device 1 manufactured by using the product name "Espansione" by KB Seiren Ltd. as the film 16 and by disposing it on the both sides of the three-dimensional knitted materials so as to cover both the two three-dimensional knitted materials 10 and 10 as illustrated in FIG. 2 (noted as "ESPANSIONE BOTH SIDES" in the figure) were stacked on the back side of the product name "Twin lumbar" by Delta Tooling and attached to the front passenger seat of a vehicle, respectively, an actual vehicle was driven, and a detection result of each of the biological signal measuring devices 1 was examined.

Figure 7A:
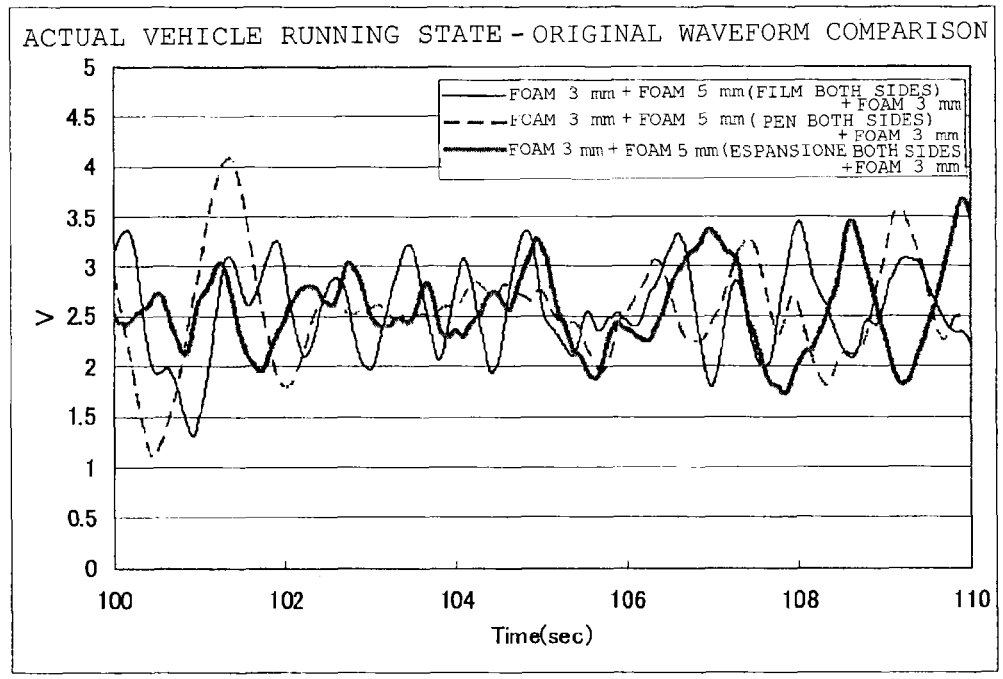
FIG. 7(A) illustrates an original waveform outputted from a microphone sensor which is a vibration sensor in a test example 4.
Figure 7B:
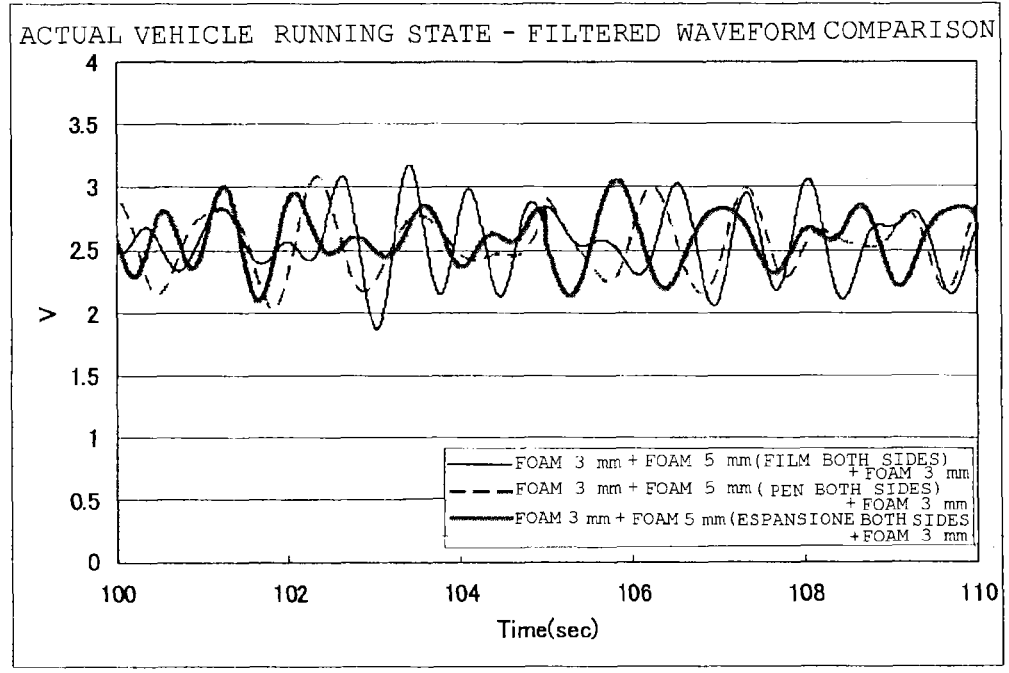
FIG. 7(B) is a diagram illustrating a waveform (filtered waveform) obtained by removing the noise such as a body motion component and the like from the original waveform by filtering.

FIG. 7(A) illustrates an original waveform outputted from the microphone sensor which is the vibration sensor 30, and FIG. 7(B) is a diagram illustrating a waveform (filtered waveform) obtained by removing the noise such as a body motion component and the like from the original waveform by filtering.

Figure 8:
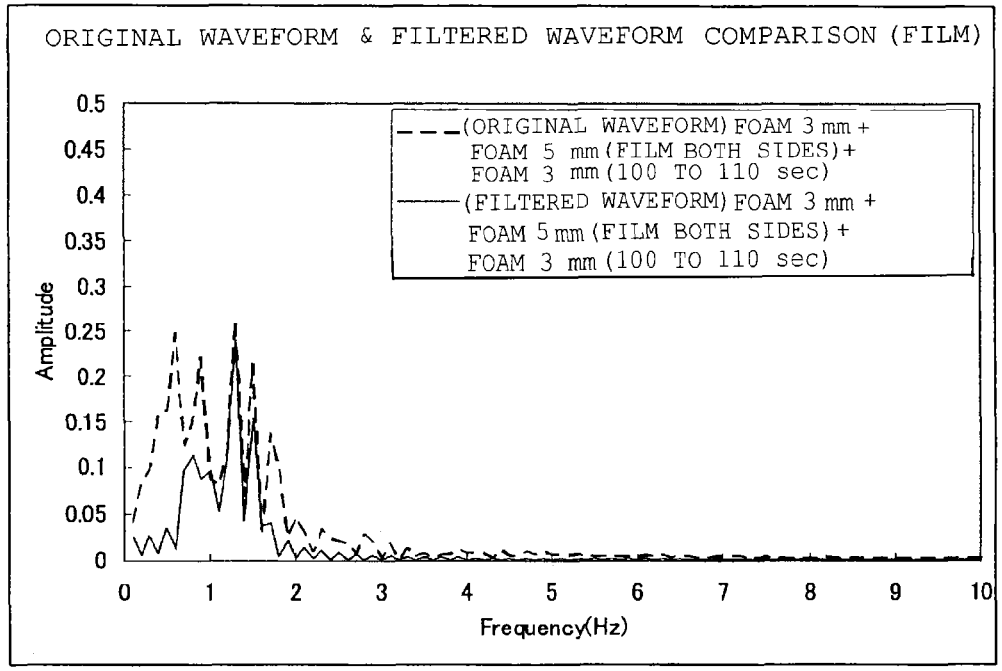
FIG. 8 is a diagram illustrating a frequency analysis result of an original waveform and a filtered waveform of a "FILM BOTH SIDE" type biological signal detector illustrated in FIGS. 7(A) and 7(B).
Figure 9:
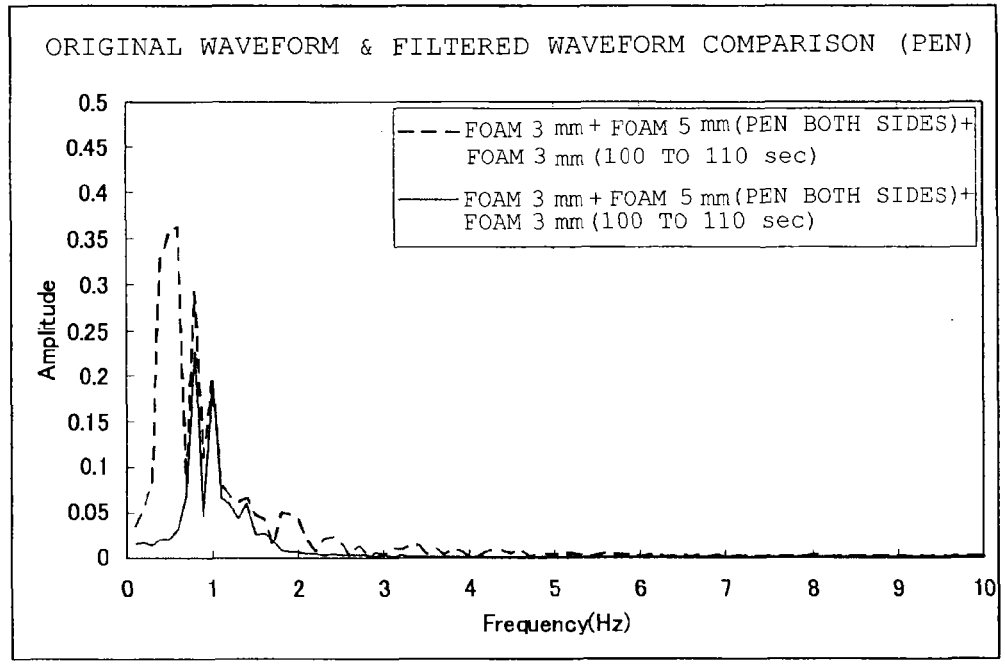
FIG. 9 is a diagram illustrating a frequency analysis result of an original waveform and a filtered waveform of a biological signal detector of a type using another film illustrated in FIGS. 7(A) and 7(B).
Figure 10:
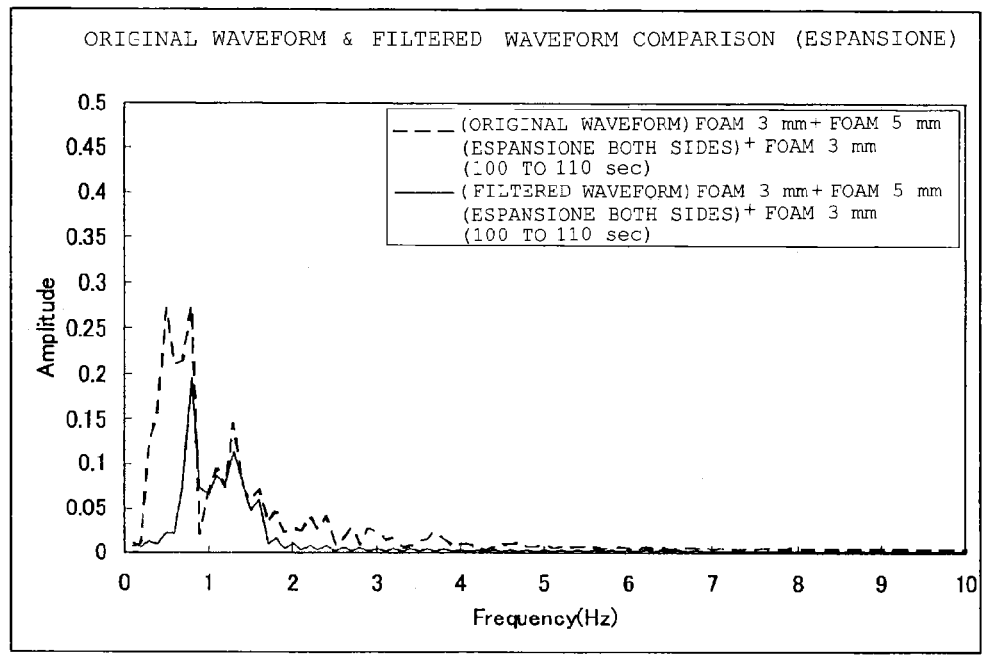
FIG. 10 is a diagram illustrating a frequency analysis result of an original waveform and a filtered waveform of a biological signal detector of a type using still another film illustrated in FIGS. 7(A) and 7(B).

FIGS. 8 to 10 are diagrams illustrating frequency analysis results of the original waveform and the filtered waveform in FIGS. 7(A) and 7(B), in which FIG. 8 illustrates a frequency analysis result using the product number "DUS605-CDR" by Sheedom Co., Ltd., FIG. 9 illustrates the result using polyethylene naphthalate (PEN) fiber by Teijin, and FIG. 10 illustrates the result using the product name "Espansione" by KB Seiren Ltd.

From FIG. 8, it can be observed that the peak of the filtered waveform is within a range of 1.2 to 1.4 Hz, and the heart rate component of this subject is reliably detected. On the other hand, in FIG. 9, there are peaks having substantially the same height in the vicinity of 0.7 to 0.8 Hz and 1.0 Hz, and FIG. 10 has a marked peak within a range of 0.8 to 0.9 Hz and a small peak in the vicinity of 1.3 Hz. In the both cases, the highest peak was shifted from the heart rate component of the subject. From this fact, it is preferable to use the product number "DUS605-CDR" by Sheedom Co., Ltd. as the film 16 in order to detect the atrial and aortic vibrations including the heart rate component of this subject, but if a frequency of a target to be sampled is different, such as when a respiration rate is to be measured, for example, or when the atrial and aortic vibrations including the heart rate during sleep with muscles in a relaxed state (both lower than that while being awake) is to be detected, those using Espansione are suitable. Moreover, it is also possible to capture the biological signal with further different frequencies by providing a plurality of types of these films in lamination. Therefore, the film 16 has a function of adjusting the resonance frequency of the biological signal measuring device 1 by varying the type and the number of disposed films.

Test Example 5

The biological signal detector 1 of the "FILM BOTH SIDES" type in the test example 4 was stacked on the back side of the product name "Twin Lumbar" by Delta Tooling and attached to a front passenger seat of a vehicle. Then, an actual vehicle was driven, and the state of the subject was measured. The result is illustrated in FIGS. 11(A) to 11(D), in which FIG. 11(D) illustrates a comprehensive determination result of the state of the subject. This is based on the technology of Japanese Unexamined Patent Application Publication No. 2009-237802 previously proposed by the applicant, in which a method (hereinafter referred to as a "zero-crossing method") in which a time-series waveform of a frequency is acquired from the time-series waveform of a detected biological signal, a time window having a predetermined time width is set, inclination of the frequency is acquired by the least square method, and the time-series waveform of the frequency is acquired by using the sign of the frequency inclination time-series waveform when the time-series waveform is outputted, the sign of an integrated waveform of the frequency inclination time-series waveform, and a point where the sign changes from positive to negative in the time-series waveform of the detected biological signal and a method (hereinafter referred to as a "peak detection method") in which the time-series waveform is subjected to smoothing differentiation and the time-series waveform is acquired by using a maximum value (peak) are used, and comparison of absolute values of the frequency inclination time-series waveforms obtained in both cases, emergence of an opposite phase when the frequency inclination time-series waveform and the time-series waveform during frequency fluctuation are outputted in a superposed manner (emergence of an opposite phase indicates a sign of sleep-onset) and the like are combined to determine the state of a person. The upper side of the vertical axis indicates a relaxed state (active state), while the degree of fatigue (fatigue state) increases toward the lower side.

In FIG. 10(D), phrases like "slightly sleepy", "dazed", "normal" and the like describe the senses felt by the subject during the test, and they substantially matched the determination result in FIG. 10(D).

Figure 11:
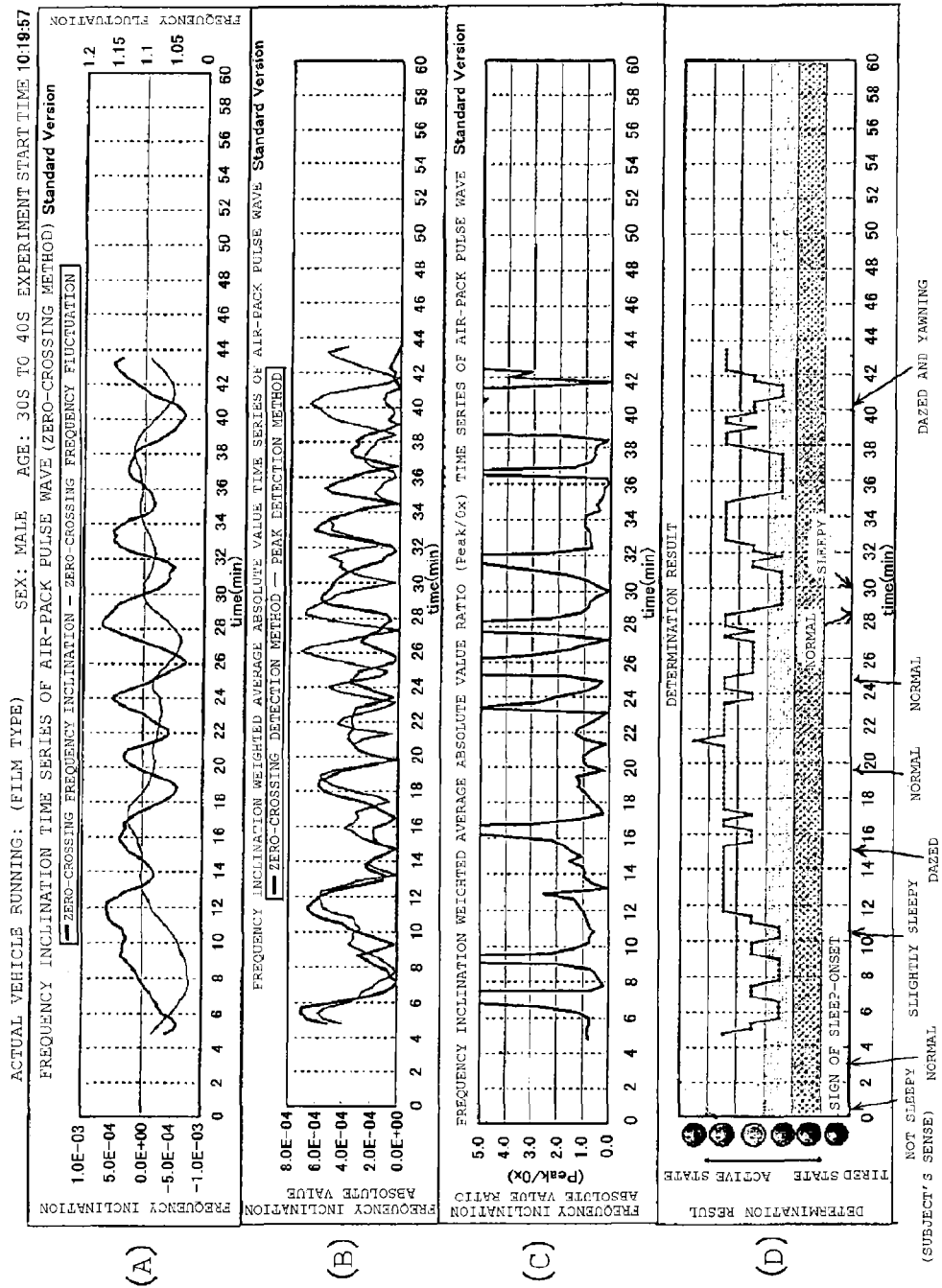
FIGS. 11(A) to 11(D) are diagrams illustrating determination results of states of subjects in an actual-vehicle running test conducted with the "film both side" type biological signal detector attached.

FIG. 11 is a result of the test conducted similarly to FIG. 10 using the biological signal detector 1 of the "PEN both sides" type in the test example 4.

As illustrated in FIG. 11(D), the determination result relatively close to the sense of the subject was also obtained in this case, but the determination result by the biological signal measuring device 1 of the above-described "film both sides" type was closer to the sense of the subject.

Figure 12:
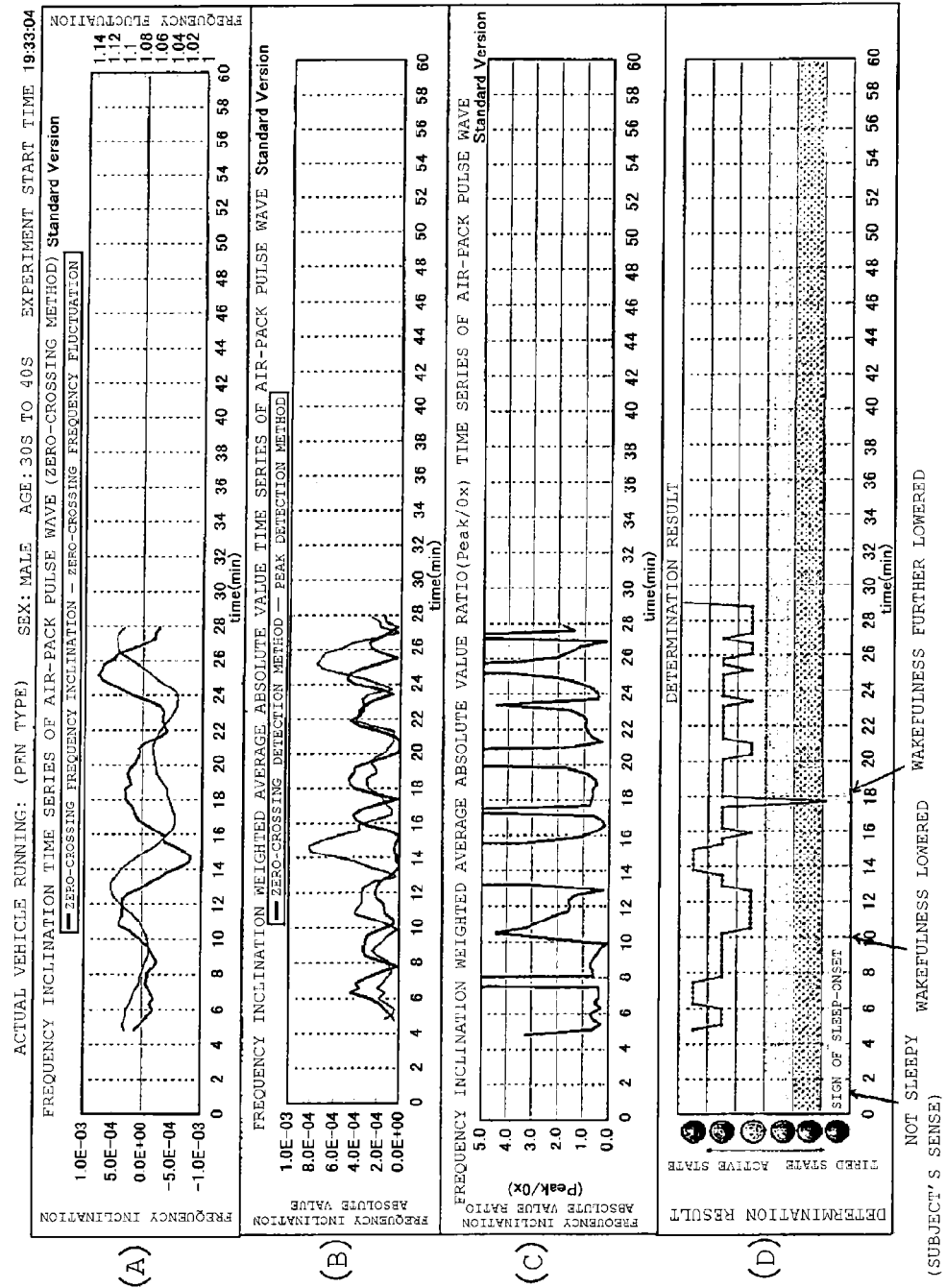
FIGS. 12(A) to 12(D) are diagrams illustrating determination results of states of subjects in the actual-vehicle running test conducted with the biological signal detector of a type using another film attached.
Figure 13:
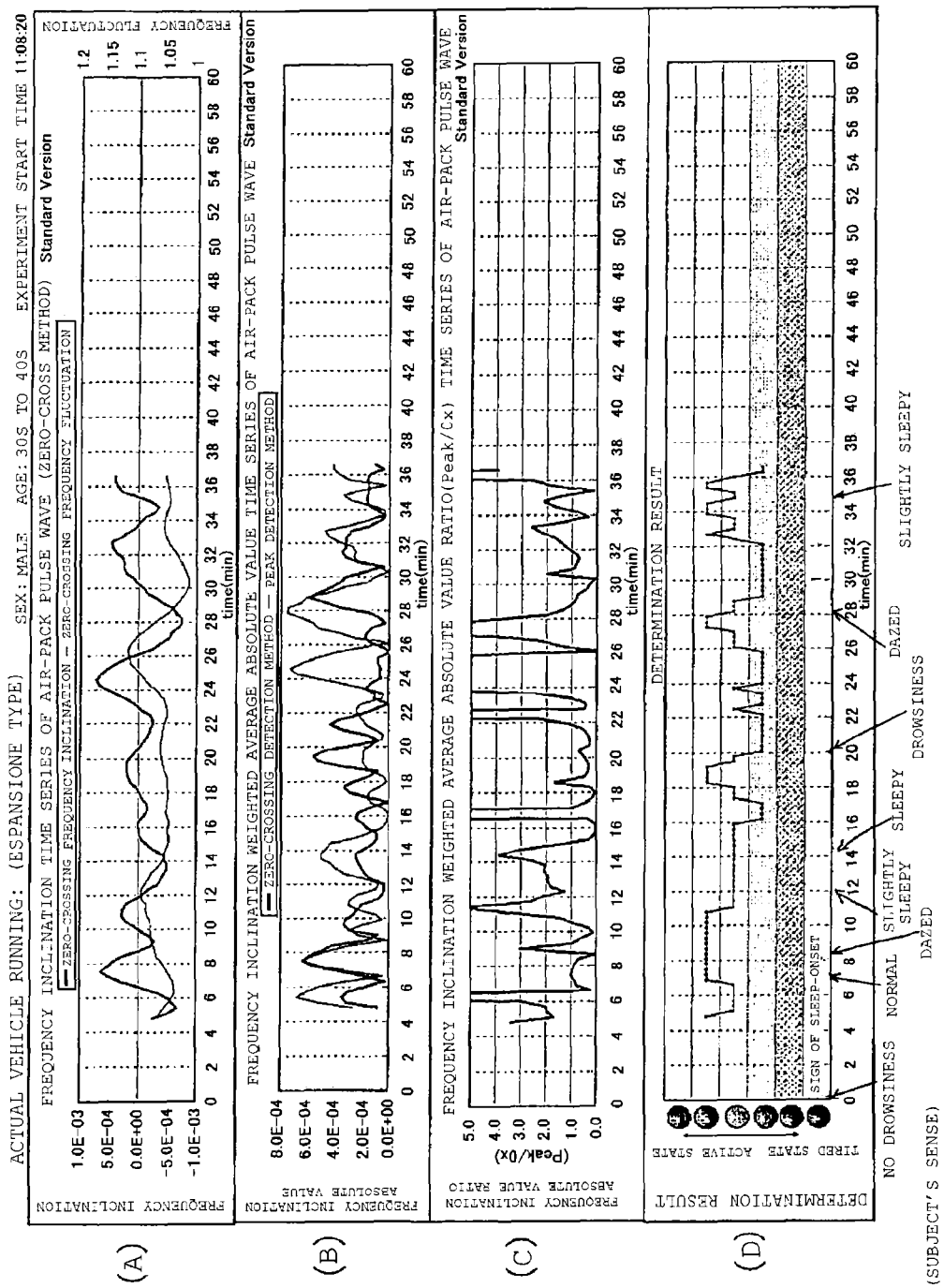
FIGS. 13(A) to 13(D) are diagrams illustrating determination results of states of subjects in the actual-vehicle running test conducted with the biological signal detector of a type using still another film attached.

FIG. 12 are a result of the test conducted similarly by using the biological signal measuring device 1 of the "Espansione both sides" type in the test example 4. Examining FIG. 12(D), there is a slight difference between the sense of the subject and the determination result in FIG. 9(D). From this fact, it can be considered that a highly elastic fiber unwoven cloth with extremely high elongation and recovery rates is not very suitable for a film when the atrial and aortic vibrations during the activity metabolism are to be captured as above. However, if a target to be sampled is different or in the case of determination of the state during sleep, use of the elastic fiber unwoven cloth like Espansione is preferable as described above.

From those facts, it is preferable that the biological signal detector 1 of the "film both sides" type is used for measurement of the biological signal during the activity metabolism and the biological signal measuring device 1 of the "PEN both sides" type or the "Espansione both sides" type is used for measurement of the biological signal during resting metabolism (relaxed state) or sleep metabolism, for example. It is needless to say that the biological signal measuring device 1 of the "PEN both sides" type or the "Espansione both sides" type might be more suitable for detection of atrial and aortic vibrations including the heart rate component depending on the subject.

The polyethylene naphthalate (PEN) fiber by Teijin itself is plastically deformed and functions as a damping element, but if a load is applied to the biological signal measuring device 1, the elasticity of the three-dimensional knitted material 10 arranged therein acts. Moreover, if the product name "Espansione" by KB Seiren Ltd. is used, since the spring elements are arranged in series by being combined with the elastic support of the three-dimensional knitted material 10, more flexible spring characteristics are created. From these facts, the biological signal measuring device 1 of the "PEN both sides" type or the "Espansione both sides" type has a resonance frequency different from that of the biological signal detector 1 of the "film both sides" type, and it is preferable to use them according to the type of a signal to be sampled or age, sex and the like of the subject. Moreover, the polyethylene naphthalate (PEN) fiber by Teijin and the product name "Espansione" by KB Seiren Ltd. are preferable since they have air permeability from the viewpoint of preventing dampness.

From the above-described results, it is found that the biological signal detector 1 of the above-described embodiment can reliably detect the biological signal of a human being as solid vibration. Moreover, since sealing performance does not have to be considered and it is only necessary to sequentially stack the plate-shaped foam bodies 21 and 22, the three-dimensional knitted materials 10 and 10, and the films 16 and 16, a manufacturing work is easy and manufacture is possible with a low cost, which is suitable for mass production.

INDUSTRIAL APPLICABILITY

The biological signal measuring device of the present invention can be used for sampling a biological signal by being attached to a range corresponding to the back part of a human being in bedding (bed, futon and the like) supporting a human body and a seat structure (a vehicle seat, a desk chair, a massaging chair, a sofa and the like).

REFERENCE SIGNS LIST

1 biological signal detector
10 three-dimensional knitted material
15 three-dimensional knitted material supporting member
15*a* through hole for arrangement
16 film
21, 22 plate-shaped foam body
30 vibration sensor

The invention claimed is:
1. A biological signal detector comprising:
   a mechanical amplification device provided with a three-dimensional knitted material for generating string vibration by vibration propagation involved in a human biological signal and a foam body on at least either one of the front side and the back side of the three-dimensional knitted material for generating membrane vibration by the vibration propagation involved in the human biological signal, and the mechanical amplification device converts the vibration involved in the human biological signal to amplified solid vibration by a superposing action of the string vibration and membrane vibration; and
   a vibration sensor attached to the mechanical amplification device for detecting the amplified solid vibration wherein
   the three-dimensional knitted material includes a pair of ground knitted fabrics arranged separately from each other and connecting yarns which reciprocate between the pair of ground knitted fabrics and connect the pair of ground knitted fabrics;
   the three-dimensional knitted material has a spring constant close to a spring constant obtained from the load-deflection characteristic of a human muscle in a load-deflection characteristic within a range of a load up to 100 N when being pressurized by a pressure plate having a diameter of 30 mm or a diameter of 98 mm;
   the foam body is a bead foam body;
   the mechanical amplification device has a film laminated between the three-dimensional knitted material and the foam body and the membrane vibration of the film is further superposed;
   the mechanical amplification device is further provided with three-dimensional knitted material supporting member in which a through hole for arrangement to arrange the three-dimensional knitted material is formed;
   in a state where the three-dimensional knitted material is arranged in the through hole for arrangement, the film is laminated on at least either one of the front side and the back side of the three-dimensional knitted material, and a peripheral edge portion is fixed to the three-dimensional knitted material supporting member; and
   the three-dimensional knitted material supporting member is a bead foam body formed having a plate shape.

2. The biological signal detector according to claim 1, wherein
   the bead foam body is a foam molded body by a bead method of a resin containing at least any one of polystyrene, polypropylene, and polyethylene.

3. The biological signal detector according to claim 1 or 2, wherein
   the bead foam body is formed having a thickness not more than an average diameter of a bead.

4. The biological signal detector according to claim 1, wherein
   the three-dimensional knitted material has a thickness larger than that of the bead foam body constituting the three-dimensional knitted material supporting member.

5. The biological signal detector according to claim 1, wherein
   the connecting yarn is a monofilament.

6. The biological signal detector according to claim 1, wherein
   the connecting yarn is a multifilament.

7. The biological signal detector according to claim 1, wherein
   a sensing portion of the vibration sensor is fixed to the three-dimensional knitted material, the foam body or the film.

8. The biological signal detector according to claim 1, wherein
   the vibration sensor is a microphone sensor.

9. The biological signal detector according to claim 1, wherein
   the biological signal detector is attached to a range corresponding to the back part of a human being in bedding or a seat structure.

10. The biological signal detector according to claim 1, wherein
   the three-dimensional knitted material has the spring constant within a range of 0.1 to 5 N/mm when being pressurized by the pressure plate having the diameter of 30 mm or the spring constant within a range of 1 to 10 N/mm when being pressurized by the pressure plate having the diameter of 98 mm.

* * * * *